(12) United States Patent
Pandey et al.

(10) Patent No.: US 9,938,283 B2
(45) Date of Patent: Apr. 10, 2018

(54) CRYSTALLINE FORM OF BARICITINIB

(71) Applicant: SUN PHARMACEUTICAL INDUSTRIES LIMITED, Mumbai, Maharashtra (IN)

(72) Inventors: Gyanendra Pandey, Faridabad (IN); Javeena, South Delhi (IN); Kaptan Singh, Gurgaon (IN); Mohan Prasad, Gurgaon (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 15/307,682

(22) PCT Filed: Apr. 29, 2015

(86) PCT No.: PCT/IB2015/053123
§ 371 (c)(1),
(2) Date: Oct. 28, 2016

(87) PCT Pub. No.: WO2015/166434
PCT Pub. Date: Nov. 5, 2015

(65) Prior Publication Data
US 2017/0204097 A1    Jul. 20, 2017

(30) Foreign Application Priority Data

May 1, 2014   (IN) .......................... 1184/DEL/2014

(51) Int. Cl.
| | | |
|---|---|---|
| *C07D 487/04* | (2006.01) | |
| *A61K 31/519* | (2006.01) | |
| *A61P 29/00* | (2006.01) | |
| *A61P 35/00* | (2006.01) | |

(52) U.S. Cl.
CPC ........ *C07D 487/04* (2013.01); *C07B 2200/13* (2013.01)

(58) Field of Classification Search
CPC .. C07D 487/04; A61K 31/519; C07B 2200/05
See application file for complete search history.

(56) References Cited

U.S. PATENT DOCUMENTS

| | | | |
|---|---|---|---|
| 8,158,616 B2 | 4/2012 | Rodgers et al. | ......... 514/210.21 |
| 2009/0233903 A1 | 9/2009 | Rodgers et al. | ......... 514/210.21 |

FOREIGN PATENT DOCUMENTS

| | | |
|---|---|---|
| WO | WO 2014/028756 | 2/2014 |
| WO | WO2014/028765 A1 | 2/2014 |

OTHER PUBLICATIONS

Bhattacharya et al. (Brittain, ed. Polymorphism in Pharmaceutical Solids, 2009, p. 334.*
USP Harmonization Stage 6:941, vol. 35(3), pp. 1-11, downloaded <http://www.usp.org/sites/default/files/usp/document/harmonization/gen-chapter/g14_pf_35_3_2009.pdf>, Nov. 23, 2016.*
International Search Report and Written Opinion for International Application No. PCT/IB2015/053123, issued by PCT dated Jul. 30, 2015.
International Preliminary Report on Patentability for International Application No. PCT/IB2015/053123, issued by PCT dated Nov. 10, 2016.
Caira, "Crystalline Polymorphism in Organic Compounds", Topics in Current Chemistry, vol. 98: 163-208 (1998).
European Extended Search Report dated Aug. 21, 2017 for EP Patent Application No. 15785897.8.

* cited by examiner

*Primary Examiner* — Susanna Moore

(57) ABSTRACT

The present invention provides a crystalline form of baricitinib characterized by an XRPD pattern substantially as depicted in FIG. 1, a process for its preparation, a pharmaceutical composition comprising it, and its use for the treatment of JAK-associated diseases.

15 Claims, 4 Drawing Sheets

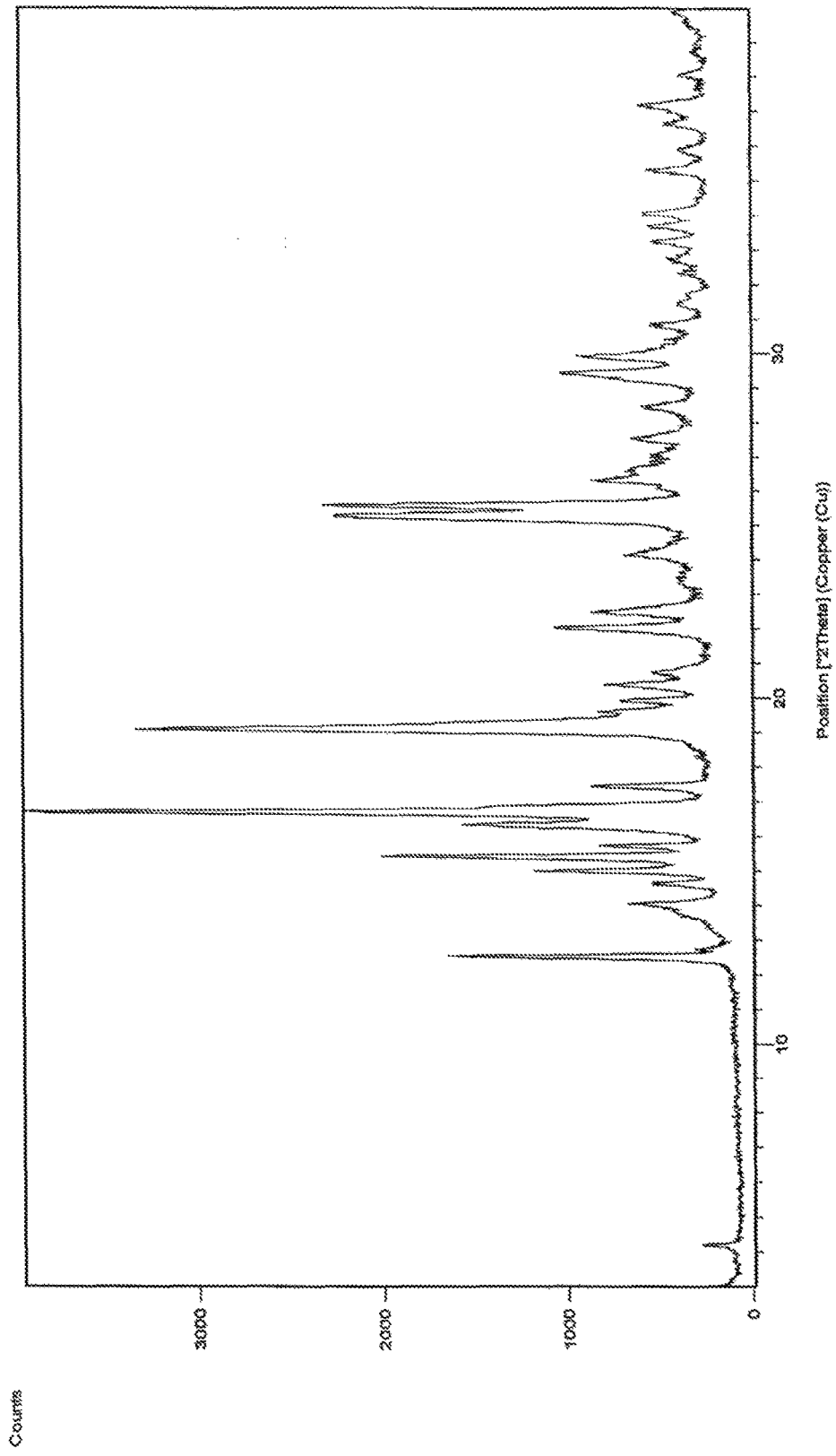
FIGURE 1: X-RAY POWDER DIFFRACTION (XRPD) PATTERN OF THE CRYSTALLINE FORM OF BARICITINIB.

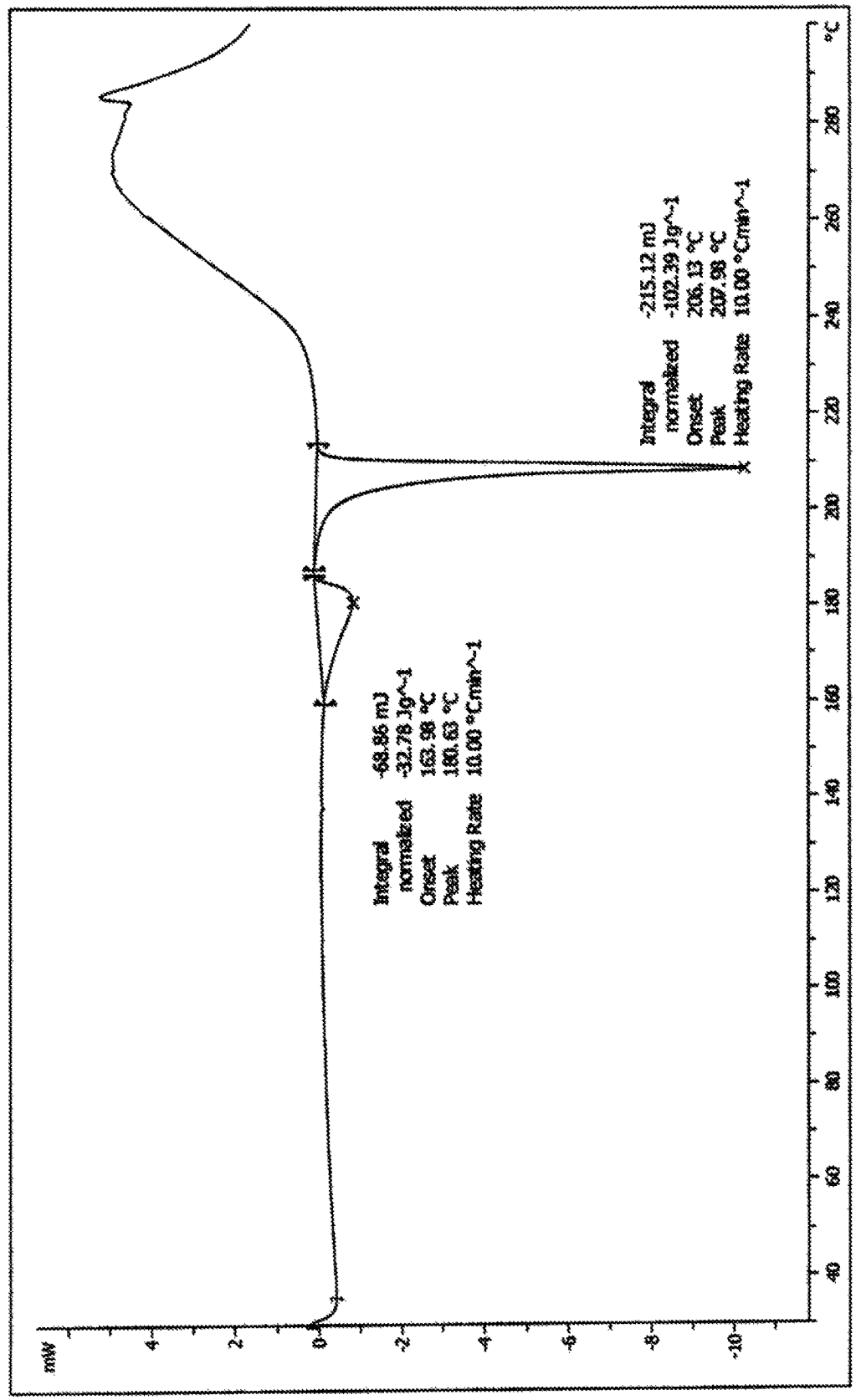
FIGURE 2: DIFFERENTIAL SCANNING CALORIMETRY (DSC) THERMOGRAM OF THE CRYSTALLINE FORM OF BARICITINIB.

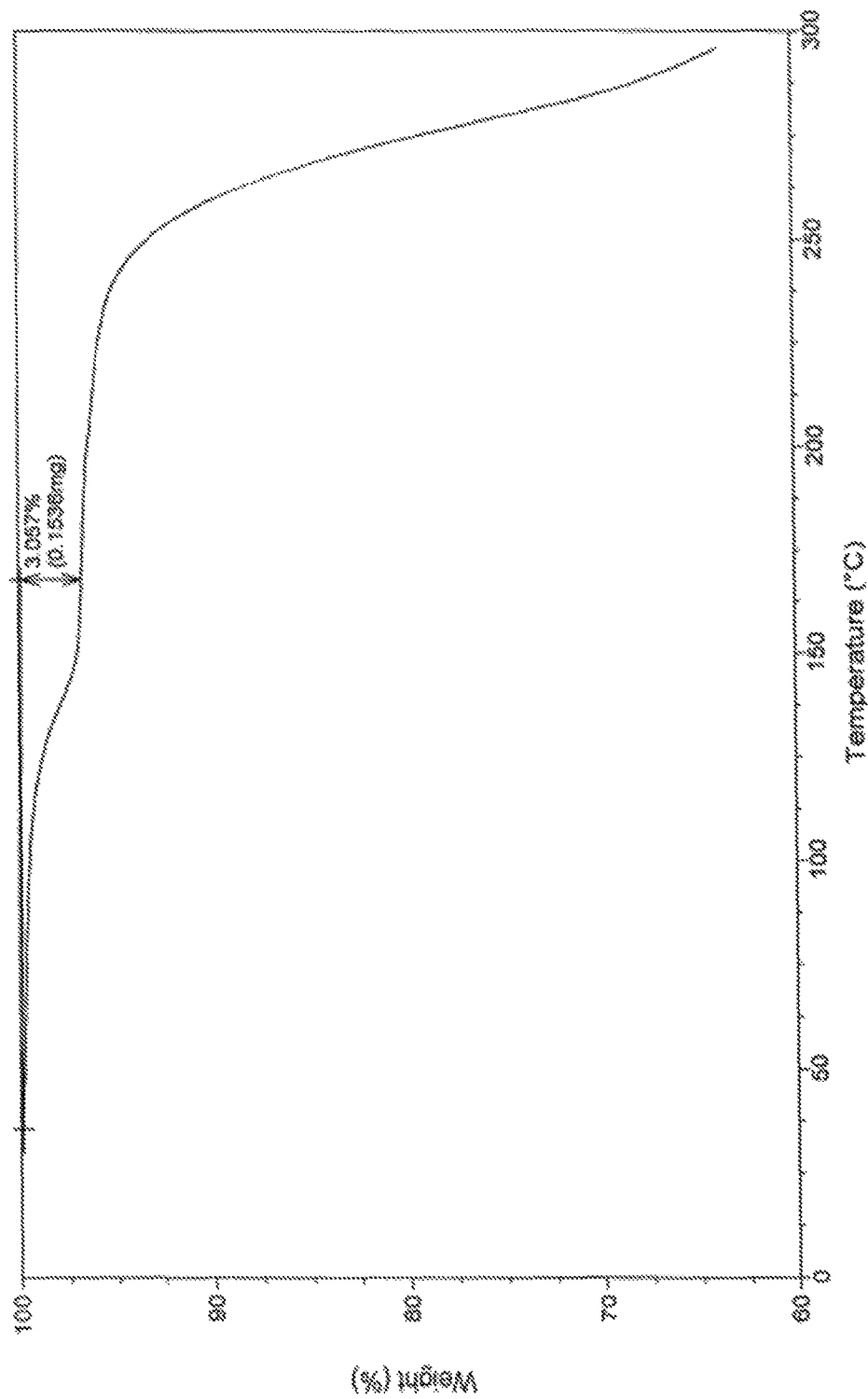
FIGURE 3: THERMOGRAVIMETRIC ANALYSIS (TGA) OF THE CRYSTALLINE FORM OF BARICITINIB.

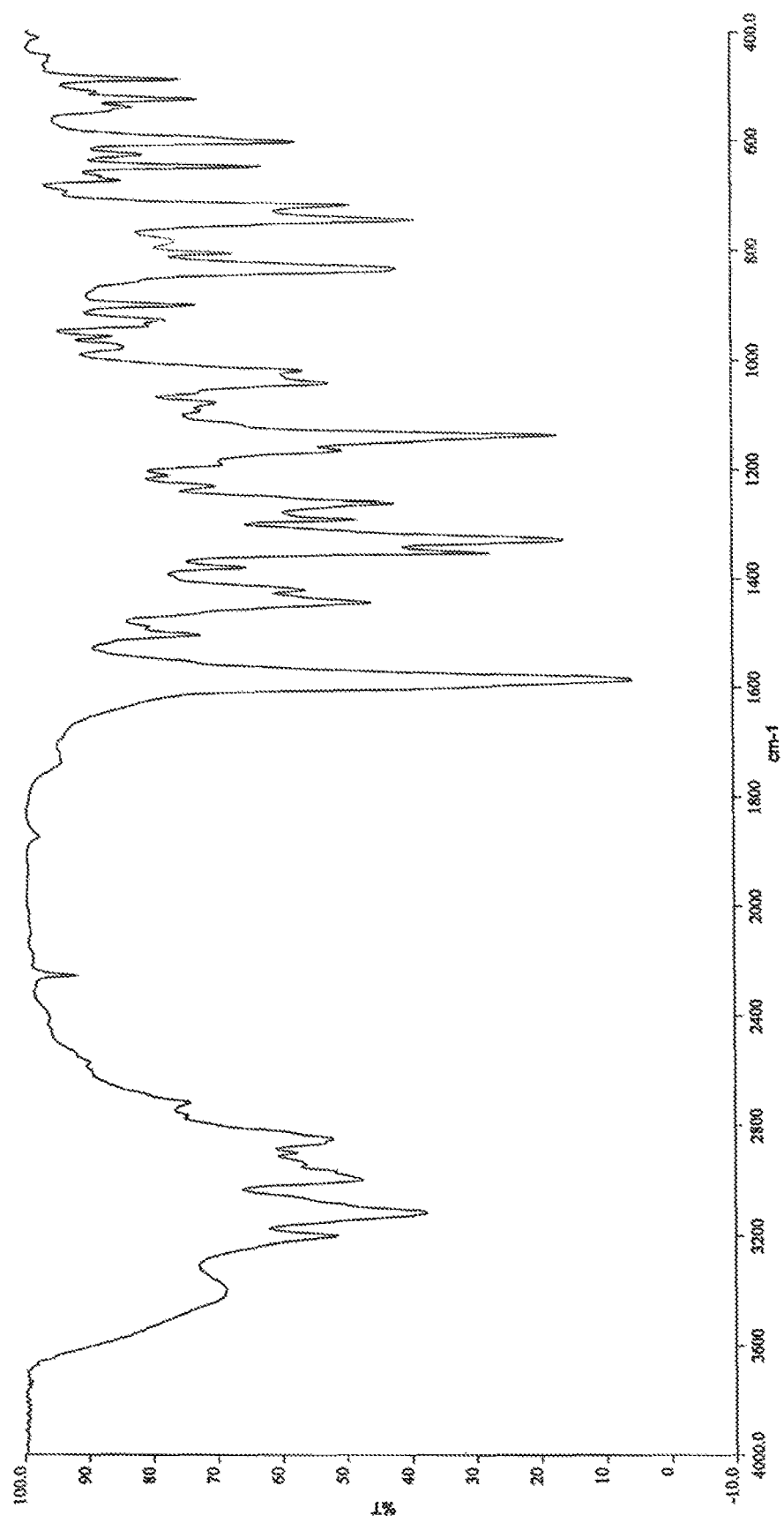
FIGURE 4: INFRA-RED (IR) SPECTRUM OF THE CRYSTALLINE FORM OF BARICITINIB.

CRYSTALLINE FORM OF BARICITINIB

FIELD OF THE INVENTION

The present invention provides a crystalline form of baricitinib, a process for its preparation, a pharmaceutical composition comprising it, and its use for the treatment of JAK-associated diseases.

BACKGROUND OF THE INVENTION

Baricitinib is a Janus Kinase (JAK) inhibitor. It is chemically designated as {1-(ethylsulfonyl)-3 -[4-(7H-pyrrolo[2,3-d]pyrimidin-4-yl)-1H-pyrazol-1-yl]azetidin-3-yl}acetonitrile, having the structure as depicted in Formula I.

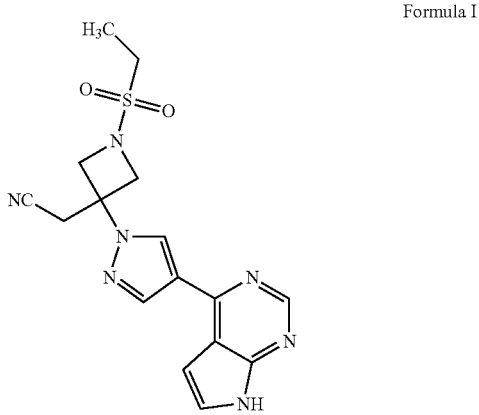 [SMILES: CCS(=O)(=O)N1CC(CC#N)(n2cc(-c3ncnc4[nH]ccc34)cn2)C1]

Formula I

Processes for the preparation of baricitinib are disclosed in U.S. Pat. No. 8,158,616.

Polymorphism, the occurrence of different crystal forms, is a property of some molecules. When polymorphism occurs, the molecules arrange themselves in two or more different ways in the crystal, giving rise to differences in crystal structures and physical properties like melting point, thermal behaviors, X-ray Powder Diffraction (XRPD) pattern, Infrared (IR) absorption fingerprint, solid state NMR spectrum, and solubility. Thus, the discovery of new polymorphic forms of a molecule is important in the development of pharmaceuticals, as they may provide materials having desirable processing properties, such as ease of handling, ease of processing, storage stability, ease of purification, improved dissolution profile, and/or improved shelf-life.

There are no reported polymorphs of baricitinib.

SUMMARY OF THE INVENTION

The present invention provides a crystalline form of baricitinib, a process for its preparation, a pharmaceutical composition comprising it, and its use for the treatment of JAK-associated diseases. The crystalline form of baricitinib is a highly pure, easy to filter, free-flowing solid with good thermodynamic stability, good solubility, residual solvent content in compliance with the ICH guidelines, prolonged shelf life, and good bioavailability.

A first aspect of the present invention provides a crystalline form of baricitinib characterized by an X-ray Powder Diffraction (XRPD) pattern having peaks at d-spacings of 5.31, 4.65, 3.52, and 3.48 Å.

A second aspect of the present invention provides a process for the preparation of a crystalline form of baricitinib characterized by an XRPD pattern having peaks at d-spacings of 5.31, 4.65, 3.52, and 3.48 Å, comprising the steps of:
i) reacting (4-(1-(3-(cyanomethyl)-1-(ethylsulfonyl)azetidin-3-yl)-1H-pyrazol-4-yl)-7H-pyrrolo[2,3-d]pyrimidin-7-yl)methyl pivalate with a base in the presence of one or more solvents;
ii) partially recovering the solvent(s) from the reaction mixture;
iii) stirring the reaction mixture;
iv) filtering the solid obtained from the reaction mixture;
v) washing the solid with a mixture of acetonitrile and water; and
vi) drying the solid.

A third aspect of the present invention provides a pharmaceutical composition comprising a crystalline form of baricitinib characterized by an XRPD pattern having peaks at d-spacings of 5.31, 4.65, 3.52, and 3.48 Å, and one or more pharmaceutically acceptable carriers, diluents, or excipients.

A fourth aspect of the present invention provides a method of treating JAK-associated diseases comprising administration to a patient a therapeutically effective amount of a composition comprising a crystalline form of baricitinib characterized by an XRPD pattern having peaks at d-spacings of 5.31, 4.65, 3.52, and 3.48 Å.

BRIEF DESCRIPTION OF THE DRAWINGS

FIG. 1: X-ray Powder Diffraction (XRPD) pattern of the crystalline form of baricitinib.
FIG. 2: Differential Scanning calorimetry (DSC) thermogram of the crystalline form of baricitinib.
FIG. 3: Thermogravimetric Analysis (TGA) of the crystalline form of baricitinib.
FIG. 4: Infra-red (IR) spectrum of the crystalline form of baricitinib.

DETAILED DESCRIPTION OF THE INVENTION

Various embodiments and variants of the present invention are described hereinafter.

The term "JAK-associated diseases," as used herein, includes inflammatory diseases, autoimmune disorders, diabetic nephropathy, and cancer.

The term "about," as used herein, refers to any value which lies within the range defined by a number up to ±10% of the value.

The crystalline form of baricitinib is characterized by an XRPD pattern having peaks at d-spacings of 5.31, 4.65, 3.52, and 3.48 Å. The crystalline form of baricitinib is further characterized by an XRPD pattern having peaks at d-spacings of 7.06, 5.91, 5.75, 5.43, and 2.98 Å. Table 1 summarizes the d-spacing values in Å, and the corresponding 2θ values of the crystalline form of baricitinib.

TABLE 1

| XRPD Peaks of the Crystalline Form of Baricitinib | | |
|---|---|---|
| Pos. [°2Th] | d-Spacing [Å] | Rel. Int. [%] |
| 4.20 | 21.00 | 5.71 |
| 10.16 | 8.71 | 0.43 |

TABLE 1-continued

XRPD Peaks of the Crystalline Form of Baricitinib

| Pos. [°2Th] | d-Spacing [Å] | Rel. Int. [%] |
| --- | --- | --- |
| 12.53 | 7.06 | 40.03 |
| 12.73 | 6.95 | 4.63 |
| 14.05 | 6.30 | 12.50 |
| 14.59 | 6.07 | 11.88 |
| 14.99 | 5.91 | 28.58 |
| 15.41 | 5.75 | 49.96 |
| 15.73 | 5.63 | 19.39 |
| 16.32 | 5.43 | 36.63 |
| 16.70 | 5.31 | 100.00 |
| 16.88 | 5.25 | 33.91 |
| 17.48 | 5.07 | 18.91 |
| 19.09 | 4.65 | 84.46 |
| 19.60 | 4.53 | 19.52 |
| 19.34 | 4.45 | 15.81 |
| 20.40 | 4.35 | 17.84 |
| 20.74 | 4.28 | 11.23 |
| 22.05 | 4.03 | 24.73 |
| 22.50 | 3.95 | 18.55 |
| 23.36 | 3.81 | 7.70 |
| 24.14 | 3.69 | 15.94 |
| 25.25 | 3.52 | 56.15 |
| 25.31 | 3.52 | 56.59 |
| 25.57 | 3.48 | 57.58 |
| 26.29 | 3.39 | 18.37 |
| 26.69 | 3.34 | 13.75 |
| 27.48 | 3.24 | 13.48 |
| 28.42 | 3.14 | 12.10 |
| 29.42 | 3.03 | 24.12 |
| 29.92 | 2.98 | 22.23 |
| 30.82 | 2.90 | 10.86 |
| 31.39 | 2.85 | 7.72 |
| 31.73 | 2.82 | 6.65 |
| 32.32 | 2.77 | 7.18 |
| 32.70 | 2.74 | 8.44 |
| 33.26 | 2.69 | 11.31 |
| 33.66 | 2.66 | 11.58 |
| 34.01 | 2.63 | 12.99 |
| 35.31 | 2.54 | 12.15 |
| 35.88 | 2.50 | 7.72 |
| 36.62 | 2.45 | 9.01 |
| 37.18 | 2.42 | 12.87 |
| 38.05 | 2.36 | 7.53 |
| 38.71 | 2.32 | 5.36 |

The crystalline form of baricitinib is further characterized by a DSC having endotherms at about 180.63° C. and about 207.98° C.

The crystalline form of baricitinib has a water content of about 3%, as determined by TGA.

The crystalline form of baricitinib is also characterized by an XRPD pattern as depicted in FIG. 1, a DSC thermogram as depicted in FIG. 2, a TGA as depicted in FIG. 3, and an IR spectrum as depicted in FIG. 4.

The preparation of the crystalline form of baricitinib is carried out by reacting (4-(1-(3-(cyanomethyl)-1-(ethylsulfonyl)azetidin-3-yl)-1H-pyrazol-4-yl)-7H-pyrrolo[2,3-d]pyrimidin-7-yl)methyl pivalate with a base in the presence of one or more solvents at a temperature of about 15° C. to 50° C., stirring the reaction mixture for about 30 minutes to about 10 hours, partially recovering the solvent(s) from the reaction mixture at a temperature of about 35° C. to about 60° C. under reduced pressure, stirring the contents at about 15° C. to 35° C. for about 5 hours to about 24 hours, filtering the solid, washing the solid with a mixture of acetonitrile and water, and drying.

The (4-(1-(3 -(cyanomethyl)-1-(ethylsulfonyl)azetidin-3-yl)-1H-pyrazol-4-yl)-7H-pyrrolo[2,3-d]pyrimidin-7-yl) methyl pivalate may be obtained by following the process disclosed in U.S. Pat. No. 8,158,616.

The base may be selected from the group consisting of inorganic and organic bases. Examples of inorganic bases include hydroxides, carbonates, and bicarbonates of alkali and alkaline earth metals. Examples of alkali and alkaline earth metal hydroxides include lithium hydroxide, sodium hydroxide, potassium hydroxide, magnesium hydroxide, calcium hydroxide, and barium hydroxide. Examples of alkali and alkaline earth metal carbonates include sodium carbonate, potassium carbonate, calcium carbonate, and magnesium carbonate. Examples of alkali metal bicarbonates include sodium bicarbonate and potassium bicarbonate. Examples of organic bases include N,N-diisopropylethylamine, triethylamine, triisopropylamine, N,N-2-trimethyl-2-propanamine, N-methylmorpholine, 4-dimethylaminopyridine, 2,6-di-tert-butyl-4-dimethylaminopyridine, 1,4-diazabicyclo[2.2.2]octane, and 1,8-diazabicyclo[5.4.0]undec-7-ene. In an embodiment of the present invention, the base used is sodium hydroxide.

The solvents may be selected from the group consisting of hydrocarbons, alcohols, ethers, chlorinated hydrocarbons, carboxylic acids, ketones, amides, sulphoxides, water, and mixtures thereof. Examples of hydrocarbons include benzene, toluene, and xylene. Examples of alcohols include methanol, ethanol, 1-propanol, 1-butanol, and 2-butanol. Examples of ethers include diethyl ether, ethyl methyl ether, di-isopropyl ether, tetrahydrofuran, and 1,4-dioxane. Examples of chlorinated hydrocarbons include dichloromethane and chloroform. Examples of carboxylic acids include formic acid, acetic acid, and propionic acid. Examples of ketones include acetone, dimethyl ketone, ethyl methyl ketone, and methyl iso-butyl ketone. Examples of amides include N,N-dimethylformamide and N,N-dimethylacetamide. Examples of sulphoxides include dimethyl sulphoxide and diethyl sulphoxide. In an embodiment of the present invention, a mixture of methanol and tetrahydrofuran is used.

In an embodiment of the present invention, the partial recovery of the solvent(s) from the reaction mixture is carried out at a temperature of about 40° C. to about 50° C. under reduced pressure.

In another embodiment of the present invention, a mixture of acetonitrile and water in a 1:2 ratio is used for washing.

Isolation of the crystalline form of baricitinib may be carried out by concentration, precipitation, cooling, filtration, centrifugation, or combinations thereof, followed by drying. Drying may be carried out using any suitable method such as drying under reduced pressure, air drying, or vacuum tray drying. Drying may be carried out at a temperature of about 35° C. to about 50° C. for about 10 hours to about 2 days.

In an embodiment of the present invention, the isolation of the crystalline form of baricitinib is carried out by filtration followed by drying at a temperature of about 35° C. to about 50° C. for about 24 hours.

The crystalline form of baricitinib is a highly pure, easy to filter, free-flowing solid. The crystalline form of baricitinib has good thermodynamic stability, good solubility, residual solvent content in compliance with the ICH guidelines, prolonged shelf life, and good bioavailability.

The crystalline form of baricitinib may be administered as part of a pharmaceutical composition for the treatment of JAK-associated diseases, including inflammatory diseases, autoimmune disorders, diabetic nephropathy, and cancer. Accordingly, in a further aspect of the present invention, there is provided a pharmaceutical composition comprising the crystalline form of baricitinib and one or more pharmaceutically acceptable carriers, diluents, or excipients, and optionally other therapeutic ingredients.

In the foregoing section, embodiments are described by way of an example to illustrate the process of the present invention. However, this is not intended in any way to limit the scope of the present invention. Several variants of the example would be evident to persons ordinarily skilled in the art which are within the scope of the present invention.

Methods

The X-ray powder diffraction patterns were recorded using a PANalytical® Expert PRO with X'celerator® as the detector, 0.02 as step size, and 3-40° 2θ as range using CuKα radiation.

The DSC thermogram was recorded using a Mettler Toledo® DSC 821e instrument.

The TGA was recorded using a TA Instruments® Q500.

The IR spectrum was recorded using a Perkin Elmer® Spectrum One FT-IR spectrometer.

Example: Preparation of Crystalline Form of Baricitinib (4-(1-(3-(Cyanomethyl)-1-(ethylsulfonyl)azetidin-3-yl)-1H-pyrazol-4-yl)-7H-pyrrolo [2,3-d]pyrimidin-7-yl)methyl pivalate (8 g), methanol (40 mL), tetrahydrofuran (160 mL), and 1M sodium hydroxide (18.4 mL) were added into a reaction vessel at 20° C. to 25° C. The reaction mixture was stirred for 3 hours. Progress of the reaction was monitored by thin layer chromatography. On completion, the reaction mixture was quenched with water (80 mL). The pH was adjusted to 7.0 to 7.5 by adding 1N hydrochloric acid. Half of the solvent was recovered at a temperature of 40° C. to 50° C. The reaction mixture was stirred at 20° C. to 25° C. for 18 hours, and then cooled to 5° C. to 10° C. The solids were filtered, washed with a mixture of acetonitrile (50 mL) and water (100 mL), and then dried at 40° C. to 50° C. under reduced pressure for 24 hours to obtain the crystalline form of baricitinib.

Yield: 70%

We claim:

1. A crystalline form of baricitinib characterized by an X-ray Powder Diffraction (XRPD) pattern obtained using CuKα radiation with a variation of ±0.2 degrees in 2θ peak values corresponding to peaks at d-spacings of 5.75, 5.31, 4.65, 3.52, and 3.48 Å.

2. The crystalline form of baricitinib according to claim 1, characterized by an XRPD pattern as depicted in FIG. 1.

3. The crystalline form of baricitinib according to claim 1, characterized by a Differential Scanning Calorimetry (DSC) thermogram having endotherms at about 180.63° C. and about 207.98° C.

4. The crystalline form of baricitinib according to claim 1, characterized by a DSC thermogram as depicted in FIG. 2.

5. The crystalline form of baricitinib according to claim 1, having a water content of about 3%, as determined by Thermogravimetric Analysis (TGA).

6. The crystalline form of baricitinib according to claim 1, characterized by a TGA as depicted in FIG. 3.

7. The crystalline form of baricitinib according to claim 1, characterized by an Infra-red (IR) spectrum as depicted in FIG. 4.

8. A process for the preparation of the crystalline form of baricitinib according to claim 1 comprising the steps of:
   i) reacting (4-(1-(3-(cyanomethyl)-1-(ethylsulfonyl)azetidin-3-yl)-1H-pyrazol-4-yl)-7H-pyrrolo[2,3-d]pyrimidin-7-yl)methyl pivalate with a base in the presence of one or more solvents;
   ii) partially recovering the solvent(s) from the reaction mixture;
   iii) stirring the reaction mixture;
   iv) filtering a solid obtained from the reaction mixture;
   v) washing the solid with a mixture of acetonitrile and water; and
   vi) drying the solid.

9. The process according to claim 8, wherein in the step (i), the base is one or more inorganic bases.

10. The process according to claim 8, wherein the one or more solvents used in step i) is selected from the group consisting of hydrocarbons, alcohols, ethers, chlorinated hydrocarbons, carboxylic acids, ketones, amides, sulphoxides, water, and mixtures thereof.

11. The process according to claim 8, wherein the partial recovery of the solvent(s) is carried out at a temperature of about 35° C. to 60° C.

12. The process according to claim 8, wherein the washing is carried out with a mixture of acetonitrile and water in a 1:2 ratio.

13. The process according to claim 8, wherein the drying is carried out at a temperature of 35° C. to 50° C.

14. A pharmaceutical composition comprising the crystalline form of baricitinib according to claim 1, and one or more pharmaceutically acceptable carriers, diluents, or excipients.

15. The process according to claim 8, wherein the base is one or more organic bases.

* * * * *